United States Patent [19]

Leazer

[11] Patent Number: 4,725,438

[45] Date of Patent: Feb. 16, 1988

[54] ALOE VERA OINTMENT

[76] Inventor: Billie S. Leazer, Rte. 14, Box 345-A, Salisbury, N.C. 28144

[21] Appl. No.: 868,374

[22] Filed: May 29, 1986

[51] Int. Cl.⁴ .............................................. A61K 35/78
[52] U.S. Cl. .................................. 424/195.1; 514/969
[58] Field of Search ..................... 424/195.1; 514/969

[56] References Cited

U.S. PATENT DOCUMENTS

| | | | |
|---|---|---|---|
| 3,892,853 | 7/1975 | Cobble | 424/195.1 |
| 4,369,180 | 1/1983 | Mihalovits | 514/2 |
| 4,481,185 | 11/1984 | Grollier et al. | 424/59 |
| 4,490,355 | 12/1984 | Desai | 424/70 |
| 4,552,755 | 11/1985 | Randen | 424/81 |
| 4,593,046 | 6/1986 | Gruber | 514/717 |

OTHER PUBLICATIONS

Chem. Abst. 98 (18): 149613h, 1983.
Chem. Abst. 101(18): 144838k, 1984.
Chem. Abst. 101(19): 157707n and 157708p, 1984.
Remington's Phar. Sci. Mock Pub. Co., Easton Pen., p. 1521, col. 1, 1980.

*Primary Examiner*—J. R. Brown
*Assistant Examiner*—John W. Rollins
*Attorney, Agent, or Firm*—Ralph H. Dougherty; James B. Hinson

[57] ABSTRACT

The invention provides an ointment useful in treating skin irritations and promoting the healing of wounds. The preferred embodiment comprises a mixture of the raw gel of the aloe vera plant with a base, such as Aquaphor. A method for making the ointment composition is also disclosed.

4 Claims, No Drawings

ALOE VERA OINTMENT

FIELD OF THE INVENTION

The invention relates to topical medications and more specifically to Aloe Ointments for treatment of wounds and other minor skin disorders.

BACKGROUND OF THE INVENTION

Aloe vera is a tropical or subtropical plant of the genus aloe. The leaves, which are lance-shaped with sharp points, contain an essentially clear viscous gel. This gel has been used for centuries by those living where the plant grows for medical purposes such as an aid in the healing of wounds and relieving other skin irritations, including treatment of minor burns.

Experience has demonstrated that maintaining the therapeutic qualities of the gel of the aloe vera plant requires that steps be taken to protect the gel from deteriorating. Typical of these protective processes is the addition of antioxidants as disclosed by U.S. Pat. No. 3,892,853. This patent, for example, describes the usefulness of the aloe gel in treating a jellyfish sting by stating that relief is total if fresh gel is used, but that if the gel is more than one and a half hours old, the gel is totally ineffective for this purpose. The reference, however, states further that fever blisters have been successfully treated with gel three weeks after extraction from the aloe vera plant, but not with gel as old as three months. Thus for some uses, freshness does not appear to be very important. However, these discussions clearly demonstrate that if the ointment is to be used in a wide range of applications, some method of protecting the freshness is required.

Aloe vera has also been used in cosmetic mixtures, as illustrated in U.S. Pat. No. 4,369,180. In this patent, the aloe vera was mixed with a wide variety of ingredients including mixtures of vitamins A, D, and E. All of these applications of the aloe vera plant either required complex processing for preparing the mixture, a wide variety of additive ingredients, or both.

The necessity for some method of protecting the gel is further described in U.S. Pat. No. 3,892,853. This patent states that at room temperature, the unprotected gel becomes rancid within twenty-four hours. In an inert atmosphere, it may remain fresh as long as five weeks. Under refrigeration, it may remain fresh only as long as six weeks.

SUMMARY OF THE INVENTION

This invention comprises an aloe ointment which is effective in treating topical wounds and other lesions. The ointment is effective, stable, and simple to prepare without requiring expensive ingredients or complicated preparation processes. The preferred embodiment of the invention is a composition of matter, which comprises a predetermined mixture of raw gel of the aloe vera plant with a base, preferably Aquaphor.

OBJECTS OF THE INVENTION

It is the principal object of this invention to provide an ointment useful in treating a wide variety of wounds and skin irritations.

It is another object of the invention to provide an aloe ointment which is stable and simple to prepare.

DESCRIPTION OF THE PREFERRED EMBODIMENT

The preferred embodiment of the invention comprises a mixture of the raw (unprocessed) gel of the aloe plant and a suitable base. The base for aloe vera ointment should mix readily with the gel of the aloe vera plant and protect the freshness of the gel for an extended period of time. The resulting mixture, comprising the aloe ointment, should have a consistency suitable for application to burns, wounds, lesions, and other skin irritations. Additionally, the base should be essentially inert, non-toxic, and have a low probability of causing adverse or allergic reactions.

Aquaphor, which is a trademark and tradename for a cholesterized, absorbent, ointment available from Belersdorf, Inc., of Norwalk, Conn., provides such a suitable base. In addition to readily mixing with the gel of the aloe vera plant, this base is relatively inexpensive. Aquaphor is a mixture of equal parts of petrolatum, mineral oil, mineral wax, and wool wax alcohol.

The ingredients of Aquaphor are readily available. Petrolatum is a neutral unctuous substance, without taste or odor derived from petroleum. Mineral oil is defined as any oil of mineral origin, such as as petroleum. Mineral wax is a mixture of hydrocarbons. Wool wax alcohol is a by-product of the cleaning and processing of wool. Thus, it will be readily appreciated that a suitable mixture of these ingredients, such as the mixture used in Aquaphor provide a suitable base for the aloe ointment.

In preparing the ointment, the gel from a suitable number of aloe vera plants is removed, using any convenient means. In preparing the aloe ointment, it has been found possible to remove the aloe gel from the leaves of the aloe vera plant by hand. This is not difficult, however, if large quantities of aloe ointment are to be prepared, other techniques for removing the gel from the leaves, such as hand pressing or roll pressing, may be more suitable. Roll pressing is accomplished by feeding the cut leaves, preferably point first, through a pair of closely spaced rolls. In order not to crush the leaves excessively, which would necessitate a filtering operation for the gel to remove such unwanted materials, it is preferable that the rolls be coated or covered with a resilient material, such as rubber, a rubber substitute, or soft plastic.

While the gel is still fresh, i.e., within five hours of removal from the aloe vera plant, and preferably within two hours of its removal, it is mixed with the Aquaphor in a ratio of from approximately 5 to about 20 percent of the gel of the aloe vera plant and from approximately 80 to about 95 percent Aquaphor. The most preferable ratio is 8% of the gel of the aloe vera plant and 92% Aquaphor. Decreasing the percentage of the aloe gel is believed to decrease the effectiveness of the ointment. Conversely, increasing the percentage of the aloe gel is believed to result in deterioration of the gel.

It has been found that this mixture is effective in relieving a wide variety of skin irritations and promoting healing of wounds. Additionally, the Aquaphor stabilizes the gel of the aloe vera plant, maintaining its effectiveness for extended periods of time.

In use, the ointment may be applied liberally to the wound, burn, or lesion to be treated. Bandages or other protective wrappings may be applied to cover the wound, if desirable. The ointment is suited for external use only, and must not be taken internally.

SUMMARY OF THE ACHIEVEMENTS OF THE OBJECTS OF THE INVENTION

From the foregoing, it is clear that I have invented an aloe ointment which is stable and simple to prepare as well as being useful in treating a wide variety of wounds, minor burns and skin irritations.

From the foregoing description of the preferred embodiment of the invention, it will be appreciated by those skilled in the art that many modifications are permitted, all of which are within the scope of the invention as described above and claimed hereinafter.

What is claimed is:

1. A stabilized ointment comprising a predetermined mixture of a cholesterized base and the gel of the aloe vera plant, said base having a composition selected such that said gel of the aloe vera plant combines with said base to form said stabilized ointment, wherein said mixture is about 80 to 95 percent by weight of said base and from about 5 to about 20 percent by weight of the gel of the aloe vera plant.

2. A stabilized ointment comprising a predetermined mixture of a cholesterized base and the gel of the aloe vera plant said base having a composition selected such that said gel of the aloe plant combines with said base to form said stabilized ointment, wherein said base is a mixture of:
   A. in the range of 25% petrolatum,
   B. in the range of 25% mineral oil,
   C. in the range of 25% wool wax alcohol, and
   D. in the range of 25% mineral wax.

3. An ointment according to claim 2 wherein said mixture by weight is in the range of 92% cholesterized base and in the range of 8% gel of the aloe vera plant.

4. An ointment in accordance with claim 3 wherein said base is a mixture of;
   A. from 20% to 30% petrolatum,
   B. from 20% to 30% mineral oil,
   C. from 20% to 30% wool wax alcohol, and
   D. from 20% to 30% mineral wax.

* * * * *